US008326431B2

(12) United States Patent  
Werder et al.

(10) Patent No.: US 8,326,431 B2  
(45) Date of Patent: Dec. 4, 2012

(54) IMPLANTABLE MEDICAL DEVICE FOR THE CONCURRENT TREATMENT OF A PLURALITY OF NEUROLOGICAL DISORDERS AND METHOD THEREFORE

(75) Inventors: Jonathan Werder, Corcoran, MN (US); Leslie A. LeMire, Shoreview, MN (US); Nina M. Graves, Minnetonka, MN (US); David C. Ullestad, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1631 days.

(21) Appl. No.: 11/414,153

(22) Filed: Apr. 28, 2006

(65) Prior Publication Data

US 2007/0255323 A1  Nov. 1, 2007

(51) Int. Cl.
A61N 1/00 (2006.01)
(52) U.S. Cl. .................................. 607/45; 607/2; 607/3
(58) Field of Classification Search .................. 607/45, 607/48, 60, 3, 2; 604/503
See application file for complete search history.

(56) References Cited

U.S. PATENT DOCUMENTS

| 3,522,811 | A | 8/1970 | Schwartz et al. |
| 3,850,161 | A | 11/1974 | Liss |
| 3,863,625 | A | 2/1975 | Viglione et al. |
| 3,967,616 | A | 7/1976 | Ross |
| 3,993,046 | A | 11/1976 | Fernandez et al. |
| 4,019,518 | A | 4/1977 | Maurer et al. |
| 4,038,536 | A | 7/1977 | Feintuch |
| 4,295,474 | A | 10/1981 | Fischell |
| 4,373,527 | A | 2/1983 | Fischell |
| 4,417,592 | A | 11/1983 | John |
| 4,566,464 | A | 1/1986 | Piccone et al. |
| 4,581,758 | A | 4/1986 | Coker et al. |
| 4,610,259 | A | 9/1986 | Cohen et al. |
| 4,692,147 | A | 9/1987 | Duggan |
| 4,702,254 | A | 10/1987 | Zabara |
| 4,944,299 | A | 7/1990 | Sulvain |
| 5,113,869 | A | 5/1992 | Napholz |
| 5,193,535 | A | 3/1993 | Bardy et al. |
| 5,269,303 | A | 12/1993 | Wernicke et al. |
| 5,284,491 | A | 2/1994 | Sutton et al. |

(Continued)

FOREIGN PATENT DOCUMENTS

EP  0 911 061 A2  4/1999

(Continued)

OTHER PUBLICATIONS

Oppenheim et al., Digital Signal Processing, Prentice Hall, Inc., Englewood Cliffs, New Jersey, 1975, pp. 18-24.
Gotman et al., "Automated Recognition and Quantification of Linterictal Epileptic Activity in the Human Scalp EEG", Electroencephalography and Clinical Neurophysiology, 1976, 41:513-529.

(Continued)

Primary Examiner — Nicole F. Lavert  
Assistant Examiner — Alyssa M Alter  
(74) Attorney, Agent, or Firm — John W. Albrecht; IPLM Group PA

(57) ABSTRACT

Implantable medical device adapted to be implanted in a patient having a plurality of neurological disorders. First and second therapy modules are adapted to provide first and second outputs to the patient for the treatment of first and second of the plurality of disorders, respectively. Also, a method for the treatment of a plurality of neurological disorders in a patient. A first output is provided to the patient for the treatment of a first one of the plurality of neurological disorders and a second output is provided to the patient for the treatment of a second one of the plurality of neurological disorders.

21 Claims, 6 Drawing Sheets

U.S. PATENT DOCUMENTS

| | | |
|---|---|---|
| 5,299,569 A | 4/1994 | Wernicke et al. |
| 5,311,869 A | 5/1994 | Okazaki |
| 5,311,876 A | 5/1994 | Olsen et al. |
| 5,335,657 A | 8/1994 | Terry, Jr. et al. |
| 5,360,437 A | 11/1994 | Thompson |
| 5,487,754 A | 1/1996 | Snell et al. |
| 5,626,145 A | 5/1997 | Clapp et al. |
| 5,626,630 A | 5/1997 | Markowitz et al. |
| 5,683,422 A | 11/1997 | Rise |
| 5,713,922 A | 2/1998 | King |
| 5,713,923 A | 2/1998 | Ward et al. |
| 5,716,377 A | 2/1998 | Rise et al. |
| 5,720,770 A | 2/1998 | Nappholz et al. |
| 5,743,860 A | 4/1998 | Hively et al. |
| 5,752,976 A | 5/1998 | Duffin |
| 5,792,186 A | 8/1998 | Rise |
| 5,832,932 A | 11/1998 | Elsberry et al. |
| 5,938,689 A | 8/1999 | Fischell et al. |
| 5,978,702 A | 11/1999 | Ward et al. |
| 5,995,868 A | 11/1999 | Dorfmeister et al. |
| 6,006,124 A | 12/1999 | Fischell et al. |
| 6,016,449 A | 1/2000 | Fischell et al. |
| 6,018,682 A | 1/2000 | Rise |
| 6,061,593 A | 5/2000 | Fischell et al. |
| 6,066,163 A | 5/2000 | John |
| 6,083,248 A | 7/2000 | Thompson |
| 6,094,598 A | 7/2000 | Elsberry et al. |
| 6,117,066 A | 9/2000 | Abrams et al. |
| 6,128,537 A | 10/2000 | Rise |
| 6,128,538 A | 10/2000 | Fischell et al. |
| 6,134,474 A | 10/2000 | Fischell et al. |
| 6,161,045 A | 12/2000 | Fischell et al. |
| 6,169,387 B1 | 1/2001 | Kalb |
| 6,176,242 B1 | 1/2001 | Rise |
| 6,185,452 B1 | 2/2001 | Schulman et al. |
| 6,200,265 B1 | 3/2001 | Walsh et al. |
| 6,205,359 B1 | 3/2001 | Bojeva |
| 6,208,894 B1 | 3/2001 | Schulman et al. |
| 6,224,549 B1 | 5/2001 | Drongelen |
| 6,227,203 B1 | 5/2001 | Rise et al. |
| 6,230,049 B1 | 5/2001 | Fischell et al. |
| 6,269,270 B1 | 7/2001 | Bojeva |
| 6,337,997 B1 | 1/2002 | Rise |
| 6,341,236 B1 | 1/2002 | Osorio et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,360,122 B1 | 3/2002 | Fischell et al. |
| 6,366,813 B1 | 4/2002 | Di Lorenzo |
| 6,374,140 B1 | 4/2002 | Rise |
| 6,427,086 B1 | 7/2002 | Fischell et al. |
| 6,459,936 B2 | 10/2002 | Fischell et al. |
| 6,466,822 B1 | 10/2002 | Pless |
| 6,473,639 B1 | 10/2002 | Fischell et al. |
| 6,480,743 B1 | 11/2002 | Kirkpatrick et al. |
| 6,529,774 B1 | 3/2003 | Greene |
| 6,560,486 B1 | 5/2003 | Osorio et al. |
| 6,591,138 B1 | 7/2003 | Fischell et al. |
| 6,597,953 B2 | 7/2003 | Boling |
| 6,597,954 B1 | 7/2003 | Pless et al. |
| 6,606,521 B2 | 8/2003 | Paspa et al. |
| 6,609,030 B1 | 8/2003 | Rezai et al. |
| 6,618,623 B1 | 9/2003 | Pless et al. |
| 6,647,296 B2 | 11/2003 | Fischell et al. |
| 6,731,984 B2 | 5/2004 | Cho et al. |
| 6,735,479 B2 | 5/2004 | Fabian et al. |
| 6,782,292 B2 * | 8/2004 | Whitehurst ............... 607/45 |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0013614 A1 | 1/2002 | Thompson |
| 2002/0049482 A1 | 4/2002 | Fabian et al. |
| 2002/0072770 A1 | 6/2002 | Pless |
| 2002/0077670 A1 | 6/2002 | Archer et al. |
| 2002/0099412 A1 | 7/2002 | Fischell et al. |
| 2002/0116042 A1 | 8/2002 | Boling |
| 2002/0169485 A1 | 11/2002 | Pless et al. |
| 2003/0004428 A1 | 1/2003 | Pless et al. |
| 2003/0028072 A1 | 2/2003 | Fischell et al. |
| 2003/0073917 A1 | 4/2003 | Echauz et al. |
| 2003/0074033 A1 | 4/2003 | Pless et al. |
| 2003/0144711 A1 | 7/2003 | Pless et al. |
| 2003/0149457 A1 | 8/2003 | Tcheng et al. |
| 2003/0176807 A1 | 9/2003 | Goetz et al. |
| 2003/0195602 A1 | 10/2003 | Boling |
| 2004/0002635 A1 | 1/2004 | Hargrove et al. |
| 2004/0068195 A1 | 4/2004 | Massicotte et al. |
| 2004/0127942 A1 | 7/2004 | Yomtov et al. |
| 2004/0133248 A1 | 7/2004 | Frei et al. |
| 2004/0138517 A1 * | 7/2004 | Osorio et al. ............... 600/9 |
| 2005/0070969 A1 | 3/2005 | Gerber |
| 2005/0119712 A1 | 6/2005 | Shafer |

FOREIGN PATENT DOCUMENTS

| | | |
|---|---|---|
| EP | 0 911 061 A3 | 11/1999 |
| EP | 1 145 735 A2 | 10/2001 |
| EP | 1 145 736 A2 | 10/2001 |
| EP | 0 904 119 B1 | 1/2004 |
| EP | 1 145 735 A3 | 4/2004 |
| EP | 1 145 736 A3 | 4/2004 |
| WO | WO 97/42990 | 11/1997 |
| WO | WO 01/97906 A | 12/2001 |
| WO | WO 2004/062470 A | 7/2004 |

OTHER PUBLICATIONS

Litt et al., "Prediction of Epileptic Seizures", 1 The Lancet Neurology May 22, 2002.

Qu et al., "A Seizure Warning System for Long-term Epilepsy Monitoring", 45 Neurology 2250, 1995.

Gotman, J., "Automatic Recognition of Epileptic Seizures in the EEG", 54 Electroencephalography and Clinical Neurophysiology at 530-540, 1982.

Lapkin et al., "The Electroencephalogram in Childhood Basilar Artery Migraine", 27 Neurology 580-583, Jun. 1977.

Murro et al., "Computerized Seizure Detection of Complex Partial Seizures", 79 Electroencephalography and Clinical Neurophysiology 330-333 (1991).

Rajna et al., "Sensory Stimulation for inhibition of Epileptic Seizures", 30(2) Epilepsia 168-174, 1989.

Lesser et al., "Brief Bursts of Pulse Stimulation Terminate Afterdischarges Caused by Cortical Stimulation", Neurology 53, Dec. 1999.

Webber, W.R.S. et al., "Automatic EEG Spike Detection: What Should the Computer Imitate", 87 Electroencephalography and Clinical Neurophysiology 330-333 (1993).

Grassberger et al., "Characterization of Strange Attractors" vol. 50, No. 5, The American Physical Society, Jan. 31, 1983.

Iasemidis et al.. "Chaos Theory and Epilepsy", The Neuroscientist, 2:118-126, 1996<retrieved from http://citeseer.ist.psu.edu/iasemidis96chaos.html.

Elger et al., "Short Communication: Seizure Prediction by Non-Linear Time Series Analysis of Brain Electrical Activity", European Journal of Neuroscience, vol. 10, pp. 786-789 (1998).

Gotman, J., "Seizure Recognition and Analysis", Montreal Neurological Institute and Department of Neurology and Neurosurgery, McGill University, Montreal, Quebec, H3A 2B4 (Canada).

Vachtsevanos et al., "Neuro-Fuzzy Approaches to Decision Making: A Comparative Study with an Application to Check Authorization", Journal of Intelligent and Fuzzy Systems, vol. 6, pp. 259-278 (1998).

Osorio, et al., "Real-Time Automated Detection and Quantitative Analysis of Seizures and Short-Term Prediction of Clinical Onset", Epilepsia, vol. 39(6), pp. 615-627 (1998).

Van Horne, Craig G. et al., "Multichannel semiconductor-based electrodes for in vivo electrochemical and electrophysiological studies in rat CNS", published in Neuroscience Letters, 120 (1990) 249-252.

Meuller, Emily E. et al., "Skin Impedance in Relation to Pain Threshold Testing by Electrical Means", published in J. Applied Physiology 5, 746-752, 1953.

Stine et al., Press Release and Letter to FDA urging that the Vagus Nerve Stimulator not be approved for treatment of depression (HRG Publication #1741) retrieved from http://www.citizen.org/publications/print-release.cfm?ID=7385.

International Search Report for PCT/US2007/002028.

* cited by examiner

IMPLANTABLE MEDICAL DEVICE FOR THE CONCURRENT TREATMENT OF A PLURALITY OF NEUROLOGICAL DISORDERS AND METHOD THEREFORE

RELATED APPLICATIONS

The present application is related to and claims from U.S. patent application Ser. No. 10/687,289, filed Oct. 15, 2003, published as U.S. Published Patent Application No. US2004/0138517 (A1), Osorio et al, Multi-Modal Operation of a Medical Device System; U.S. Provisional Patent Application No. 60/503,998, filed Sep. 19, 2003; and U.S. Provisional Patent Application No. 60/418,553, filed Oct. 15, 2002.

FIELD

The present invention relates to devices and methods for the detection and the treatment of nervous system disorders.

BACKGROUND

Nervous system disorders, including neurological, disorders, affect millions of people, causing death and a degradation of life. Nervous system disorders include disorders of the central nervous system, peripheral nervous system, and mental health and psychiatric disorders. Such disorders include, for example without limitation, epilepsy, Parkinson's disease, essential tremor, dystonia, and multiple sclerosis (MS). Additionally, nervous system disorders include mental health disorders and psychiatric disorders which also affect millions of individuals and include, but are not limited to, anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (narcolepsy), obesity, and anorexia. As an example, epilepsy is the most prevalent serious neurological disease across all ages. Epilepsy is a group of neurological conditions in which a person has or is predisposed to recurrent seizures. A seizure is a clinical manifestation resulting from excessive, hypersynchronous, abnormal electrical or neuronal activity in the brain. (A neurological event is an activity that is indicative of a nervous system disorder. A seizure is a type of a neurological event.) This electrical excitability of the brain may be likened to an intermittent electrical overload that manifests with sudden, recurrent, and transient changes of mental function, sensations, perceptions, and/or involuntary body movement. Because the seizures are unpredictable, epilepsy affects a person's employability, psychosocial life, and ability to operate vehicles or power equipment. It is a disorder that occurs in all age groups, socioeconomic classes, cultures, and countries. In developed countries, the age-adjusted incidence of recurrent unprovoked seizures ranges from 24/100,000 to 53/100,000 person-years and may be even higher in developing countries. In developed countries, age specific incidence is highest during the first few months of life and again after age 70. The age-adjusted prevalence of epilepsy is 5 to 8 per 1,000 (0.5% to 0.8%) in countries where statistics are available. In the United States alone, epilepsy and seizures affect 2.3 million Americans, with approximately 181,000 new cases occurring each year. It is estimated that 10% of Americans will experience a seizure in their lifetimes, and 3% will develop epilepsy by age 75.

There are various approaches in treating nervous system disorders. Treatment therapies can include any number of possible modalities alone or in combination including, for example, electrical stimulation, magnetic stimulation, drug infusion, and/or brain temperature control.

Several devices have been disclosed for the treatment of a neurological disorder. Examples of such devices include U.S. Pat. No. 5,832,932, Elsberry, Method of Treating Movement Disorders By Brain Infusion, which discloses techniques and apparatus for infusing drugs into the brain to treat movement disorders resulting in abnormal motor behavior. An implantable pump and a catheter, the catheter having a proximal end coupled to the pump and a discharge portion for placement adjacent a predetermined infusion site in the brain for infusing therapeutic dosages of the one or more drugs into the brain. The pump is operated to discharge a predetermined dosage of the one or more drugs through the discharge portion of the catheter into the infusion site. A sensor may be used in combination with the implantable pump and catheter, whereby the sensor generates a signal relating to the extent of the abnormal motor behavior. The therapeutic dosage is regulated so that the dosage is adjusted in response to an increase in the abnormal behavior to decrease the abnormal motor behavior.

U.S. Pat. No. 6,591,138, Fischell, Low Frequency Neurostimulator For the Treatment of Neurological Disorders, discloses a system for treating neurological conditions by low frequency time varying electrical stimulation includes an electrical device for applying such low-frequency energy, in a range below approximately 10 Hertz, to the patient's brain tissue. An implantable embodiment applies direct electrical stimulation to electrodes implanted in or on the patient's brain, while a non-invasive embodiment causes a magnetic field to induce electrical currents in the patient's brain.

U.S. Pat. No. 6,609,030, Rezai, Method of Treating Psychiatric Diseases By Neruomodulation Within the Dorsomedial Thalamus, discloses a method for treating psychiatric diseases such as Affective Disorder (including Major Depression and Bipolar Disorder), Anxiety Disorder (including General Anxiety Disorder, Obsessive Compulsive Disorder and Panic Disorder) by stimulation (either electrical and/or chemical) of the thalamus, and in particular a region within the dorsomedial nucleus of the thalamus. The method includes the steps of determining a common group of patients, each suffering from a common specific diagnosis or a psychological disorder; determining which common region of the patients' thalami are involved in carrying the pathological electrical signals and/or metabolic activity which may otherwise be generated in dissimilar and disparate regions of the brains of the patients; surgically implanting an electrode and/or catheter and electrical signal generating device and/or drug pump such that the electrode and/or catheter is positioned within the region of the thalamus identified as the dorsomedial nucleus; and selectively adjusting the level of electrical and/or chemical stimulation in accordance with the specific effect of the stimulation of the patient. In particular, the region of the thalamus most frequently associated with the aforementioned psychiatric disease is the dorsomedial nucleus.

U.S. Published Patent Application No. 2004/0002635, Hargrove, Method and Apparatus For Utilizing Amplitude-Modulated Pulse-Width Modulation Signals For Neurostimulation and Treatment of Neurological Disorders Using Electrical Stimulation, discloses a computing device-controlled system is described for the generation of amplitude-modulated pulse-width modulation (AMPWM) signals for use in treating neurological dysfunction via cranial neurostimulation, where the AMPWM signal is specifically designed to minimize the electrical impedance of the tissues of the head. A low-frequency carrier signal is determined for the AMPWM signal by measuring EEG activity at a reference site or sites, generally corresponding with the location of suspected brain dysfunction. Carrier signal frequency is variably related to critical frequency components of the EEG power spectral density, determined from statistical analysis of amplitudes and variability, and dynamically changed as a function of time to prevent entertainment. The AMPWM signal is presented to a subject via a plurality of neurostimulation delivery modes for therapeutic use.

Devices and methods have also been developed to sense a condition and then respond with a treatment for a certain neurological disorder. For example, U.S. Pat. No. 6,647,296, Fischell et al, Implantable Apparatus For Treating Neurological Disorders, discloses a multiple electrode, closed-loop, responsive system for the treatment of certain neurological diseases such as epilepsy, migraine headaches and Parkinson's disease. Brain electrodes would be placed in close proximity to the brain or deep within brain tissue. When a neurological event such as the onset of an epileptic seizure occurs, EEG signals from the electrodes are processed by signal conditioning means in a control module that can be placed beneath the patient's scalp, within the patient's scalp, or situated externally on the patient. Neurological event detection means in the control module will then cause a response to be generated for stopping the neurological event. The response could be an electrical signal to brain electrodes or to electrodes located remotely in the patient's body. The response could also be the release of medication or the application of a sensory input such as sound, light or mechanical vibration or electrical stimulation of the skin. The response to the neurological event can originate from devices either internal or external to the patient. The system also has the capability for multi-channel recording of EEG related signals that occur both before and after the detection of a neurological event. Programmability of many different operating parameters of the system by means of external equipment provides adaptability for treating patients who manifest different symptoms and who respond differently to the response generated by the system.

Examples in the cardiac field include U.S. Pat. No. 6,731,984, Cho et al, Method For Providing A Therapy To a Patient Involving Modifying the Therapy After Detecting an Onset of Sleep in the Patient and Implantable Medical Device Embodying Same; U.S. Pat. No. 5,284,491, Sutton et al, Cardiac Pacemaker With Hysteresis Behavior; and U.S. Pat. No. 5,193,535, Bardy et al, Method and Apparatus For Discrimination of Ventricular Tachycardia From Ventricular Fibrillation and For Treatment Thereof.

Cho et al '984 discloses an implantable medical device system is described including an implantable medical device for implantation in a patient. One embodiment of the implantable medical device includes a therapy component for providing a therapy to the patient, a minute ventilation (MV) sensing circuit producing MV values indicative of a MV of the patient at time intervals, and computational circuitry. The computational circuitry receives a number of the MV values over a period of time, calculates a statistical parameter (e.g., a mean) of the MV values, and calculates a deviation of the MV values from the statistical parameter (e.g., a standard deviation of the MV values). The computational circuitry detects an onset of sleep in the patient when the deviation of the MV values from the statistical parameter is less than a predetermined MV threshold value, and signals the therapy component to modify the therapy when the onset of sleep is detected in the patient. A method is disclosed for providing therapy to a patient, including detecting an onset of sleep in the patient, and modifying the therapy following the detecting the onset of sleep in the patient.

Sutton et al '491 discloses a pacemaker having a hysteresis feature which permits intrinsic heart activity, controlled by the sinus node to resume optimally after pacing. The pacemaker has a programmable lower rate and upper rate, a programmable lower hysteresis rate (LRH) corresponding to a lower rate hysteresis interval (LRHI), and a programmable rate (IR) intermediate an upper pacing rate (UR) and a lower pacing rate (LR). A microprocessor measures the average rate of change MAVG in the intervals between consecutive ventricular depolarizations, and compares the last intrinsic escape interval RRN to the lower rate hysteresis interval (LRHI). If the last intrinsic escape interval RRN is longer than the lower rate hysteresis interval (LRHI), and if the value of MAVG is greater than a first preselected value SLI but less than a second preselected value SL2, the pacemaker stimulates at the lower rate hysteresis (LRH) and thereafter gradually increases the pacing rate up to the intermediate rate (IR). A time counter maintains a continuous pacing at the intermediate rate (IR) for a predefined period of time, and the pacing rate is gradually decreased toward the lower pacing rate (LR).

Bardy et al '535 discloses an implantable cardioverter/defibrillator provided with method and apparatus for discrimination between ventricular tachycardia and ventricular fibrillation. The device is provided with two pairs of electrodes, each pair of electrodes coupled to processing circuitry for identifying a predetermined fiducal point in the electrical signal associated with a ventricular depolarization. The cumulative beat to beat variability of the intervals separating the two identified fiducal points, over a series of detected depolarizations is analyzed. The result of this analysis is used to distinguish between ventricular tachycardia and ventricular fibrillation.

Devices and methods have also been developed that provide multiple treatments for a single disorder. An example is U.S. Pat. No. 6,094,598, Elsberry, Method of Treating Movement Disorders By Brain Stimulation and Drug Infusion, which discloses techniques using one or more drugs and electrical stimulation for treating neural disorders, including movement disorders resulting in abnormal motor response, by means of an implantable signal generator and electrode and an implantable pump and catheter. A sensor is used to detect activity resulting from the neural disorder. A microprocessor algorithm analyzes the output from the sensor in order to regulate the stimulation and drug dosage delivered to the neural tissue.

Also, U.S. Pat. No. 5,713,923, Ward et al, Techniques For Treating Epilepsy By Brain Stimulation and Drug Infusion, U.S. Pat. No. 5,578,702, Ward et al, Techniques For Treating Epilepsy By Brain Stimulation and Drug Infusion, disclose techniques using one or more drugs and electrical stimulation for treating a neurological disorder, including epilepsy, by means of an implantable signal generator and electrode and an implantable pump and catheter. A sensor is used to detect a seizure or symptoms resulting from the onset of a seizure. A microprocessor algorithm analyzes the output from the sensor in order to regulate the stimulation and drug dosage delivered to the neural tissue.

U.S. Pat. No. 6,176,242, Rise, Method of Treating Manic Depression By Brain Infusion, discloses techniques using one or more drugs, electrical stimulation or both to treat depression or manic depression by means of an implantable signal generator and electrode and/or an implantable pump and catheter. A catheter is surgically implanted in selected sites in the brain to infuse the drugs, and one or more electrodes are surgically implanted in the brain at selected sites to provide electrical stimulation.

U.S. Published Patent Application No. US2004/0138517 (A1), Osorio et al, Multi-Modal Operation of a Medical Device System, discloses multi-modal operation for the treatment of a nervous system disorder. The medical device system supports both a first feature and a second feature associated with treatment therapy with an implanted component and an external component and may support a plurality of features during a treatment interval.

SUMMARY

Singular among the devices and methods noted above is that all involve the treatment of a single disorder, even though multiple treatments may be applied to that single disorder. Such devices and methods then are ill-equipped and not configured to effectively treat or respond to multiple disorders within a single patient.

Many neurological disorders are co-morbidities. For example, sufferers of migraine headache are often also diagnosed with clinical depression. Likewise, epilepsy patients have a high occurrence of clinical depression as well as severe headache. Implantable medical devices have long been considered for the treatment of neurological disorders. However, these implantable medical devices are designed to treat a single disorder, often leaving the concurrent disorder untreated or, perhaps, left to rely on unrelated medication. Embodiments of the present invention provide an implantable medical device capable of concurrently treating two or more neurological disorders.

In an embodiment, the present invention provides an implantable medical device adapted to be implanted in a patient having a plurality of neurological disorders. A first therapy module is adapted to provide a first output to the patient for the treatment of a first one of the plurality of disorders. A second therapy module is adapted to provide a second output to the patient for the treatment of a second one of the plurality of disorders.

In an embodiment, at least one of the first therapy module and the second therapy module is operative in a closed loop.

In an embodiment, the at least one of the first output and the second output is a function of another of the first output and the second output.

In an embodiment, a sensor is adapted to detect a sensed event from the patient associated with at least one of the plurality of neurological disorders and at least one of the first therapy module and the second therapy module is operatively coupled to the sensor and being responsive to a sensed event from the patient.

In an embodiment, the first therapy module is a drug delivery module and wherein the first output is the delivery of a medicament.

In an embodiment, the second therapy module is an electrical stimulator module and wherein the second output is an electrical stimulus signal.

In an embodiment, at least one of the drug delivery module and the electrical stimulator module is operative in a closed loop responsive to the other of the drug delivery module and the electrical stimulator module.

In an embodiment, a sensor is adapted to detect a sensed event from the patient, and at least one of the drug pump module and the electrical stimulator module is operatively coupled to the sensor and responsive to a sensed event from the patient.

In an embodiment, the present invention provides a method for the treatment of a plurality of neurological disorders in a patient using an implantable medical device having a first therapy module and a second therapy module. A first output from the first therapy module is provided to the patient for the treatment of a first one of the plurality of neurological disorders. A second output from the second therapy module is provided to the patient for the treatment of a second one of the plurality of neurological disorders.

In an embodiment, at least one of the first therapy module and the second therapy module is operated in a closed loop.

In an embodiment, the at least one of the first output and the second output being a function of another of the first output and the second output.

In an embodiment, a sensed event is detected from the patient associated with at least one of the plurality of neurological disorders and operating at least one of the first therapy module and the second therapy module responsive to the sensed event.

In an embodiment, the first therapy module is a drug delivery module and wherein the first output is the delivery of a medicament.

In an embodiment, the second therapy module is an electrical stimulator module and the second output is an electrical stimulus signal.

In an embodiment, at least one of the drug delivery module and the electrical stimulator module is operated in a closed loop being responsive to the other of the drug delivery module and the electrical stimulator module.

In an embodiment, a sensed event is detected from the patient and wherein at least one of the drug pump module and the electrical stimulator module is responsive to the sensed event.

In an embodiment, the implantable medical device is implanted in the patient.

DRAWINGS

DETAILED DESCRIPTION

The entire content of U.S. Published Patent Application No. US2004/0138517 (A1), Osorio et al, Multi-Modal Operation of a Medical Device System, is hereby incorporated by reference. In aspects of the present invention, the multi-modal operation of the medical device system disclosed in Osorio et al '517 would be applied to the treatment of multiple neurological disorders.

Figure 1:
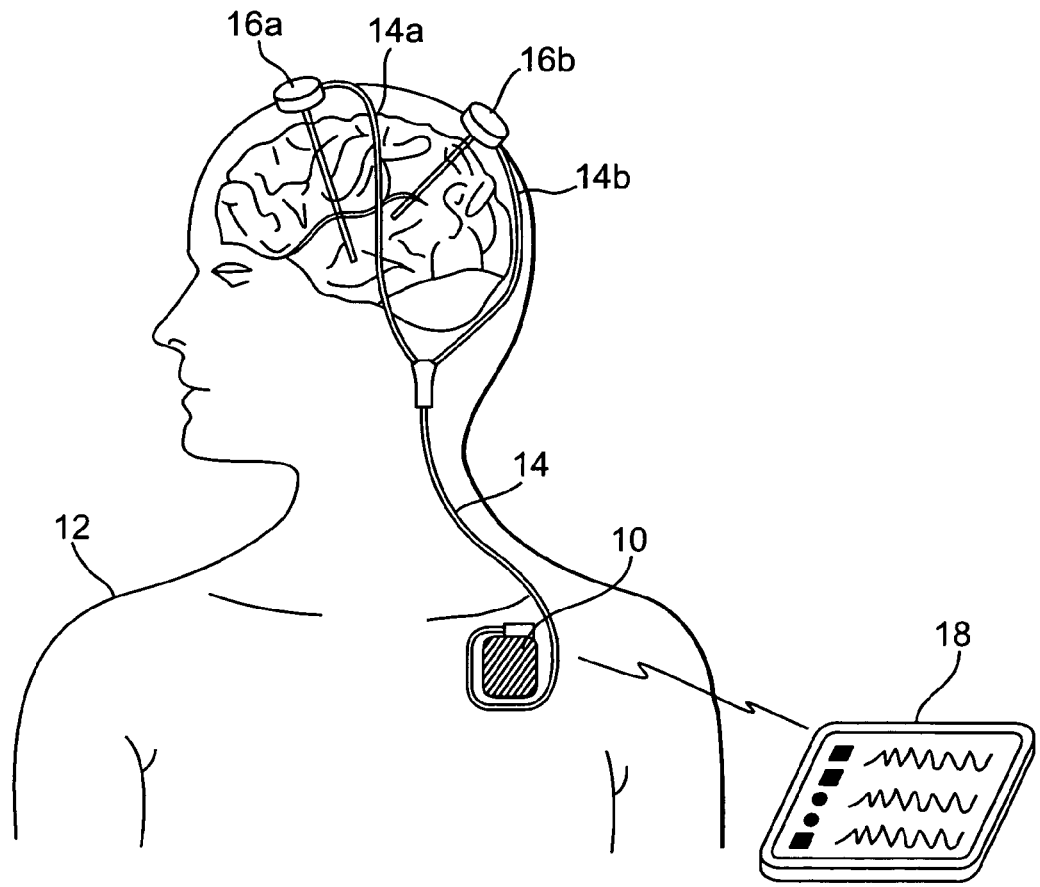
FIG. 1 illustrates a pectorally implanted neurological stimulator having two electrodes implanted in the cranium.

FIG. 1 illustrates implantable medical device 10 implanted in the pectoral region of patient 12. Lead 14, which is split into leads 14a and 14b, couples medical device 10 with electrodes 16a and 16b. Medical device 10, programmed by external programmer 18, may deliver a first treatment to electrode 16a for one neurological disorder and a second treatment to electrode 16b for another neurological disorder.

Medical device 10 may deliver two different treatment therapies to two different electrodes (16a and 16b) placed in differing neurological locations for the treatment of multiple neurological disorders.

Treatment therapy for an individual neurological disorder is conventional and may not significantly differ from the treatment provided by a medical driving only one active electrode and having only one treatment modality. That is, known treatment therapies for a single neurological disorder, e.g., epilepsy, may be employed as one treatment therapy applied to one of the electrodes, e.g., electrode 16a, of medical device 10 for a first neurological disorder. Similarly, a different, but still known, treatment therapy may be concurrently employed as a second treatment therapy applied to another of the electrodes, e.g., electrode 16b, of medical device 10 for a second neurological disorder. In the medical device illustrated in FIG. 1, both treatment therapies are electrical stimulation therapies. However, it is to be recognized and understood one or both treatment therapies could be drug infusion therapies or other therapies instead of or in addition to electrical stimulation therapy.

Figure 2:
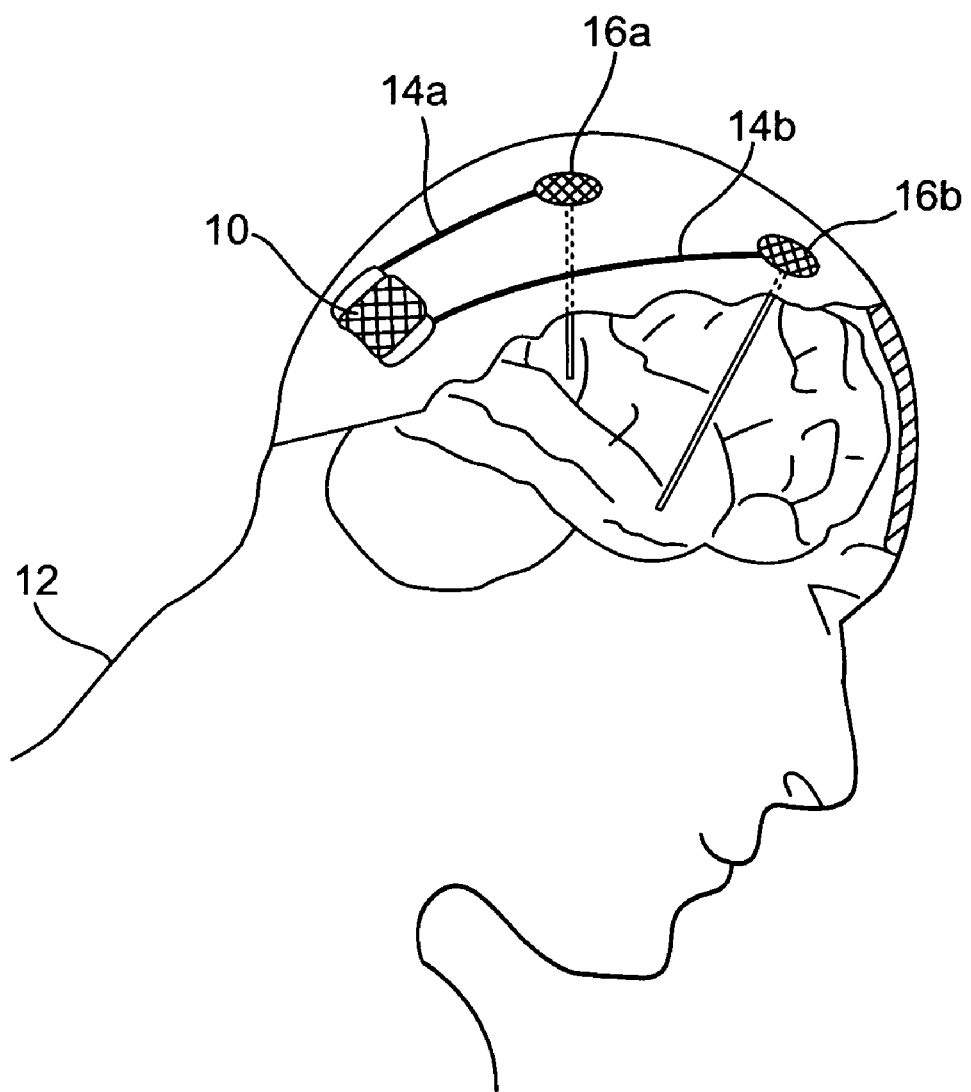
FIG. 2 illustrates a cranial implanted neurological stimulator having two electrodes.

Alternatively, implantable medical device 10 may be implanted under the scalp or in the cranium as illustrated in FIG. 2. External programmer 18 (not shown in FIG. 2) would also be used with medical device 10 in FIG. 2.

Leads 14, 14a and 14b are operatively coupled to medical device 10 and may be routed through the neck, just under the skin to the skull. The distal end of each lead (14 or 14a and 14b) may be inserted through a cranial burr hole and into a specific target of the brain of interest for treatment of a particular neurological disorder. The distal end of leads 14 or 14a and 14b terminate in electrodes 16a and 16b, or alternatively, any combination of output ports and/or thermal transducers. In this of multiple treatment for epilepsy and depression, the distal end of one electrode, e.g., electrode 16a, may be located in a region of the brain that when therapy is applied reduces seizures and the distal end of another electrode, e.g., electrode 16b, may be located in a region of the brain that when therapy is applied symptoms of depression are reduced.

Leads 14, electrodes 16 and/or other wires may be employed for use as therapy outputs of medical device 10, e.g., at least one pair of electrodes, a catheter output port and/or a thermal transducer. Leads 14, electrodes 16 and/or other wires may also be employed for sensing functions, e.g., an electrode 16 may be employed for sensing electrical activity of the brain. Leads 14, electrodes 16 and/or other wires may also be employed as an extension to another lead 14, electrode 16 and/or other wire. Leads 14, electrodes 16 and/or other wires may also be employed to furcate other leads 14, electrodes 16 and/or other wires to access multiple targets.

Figure 3:
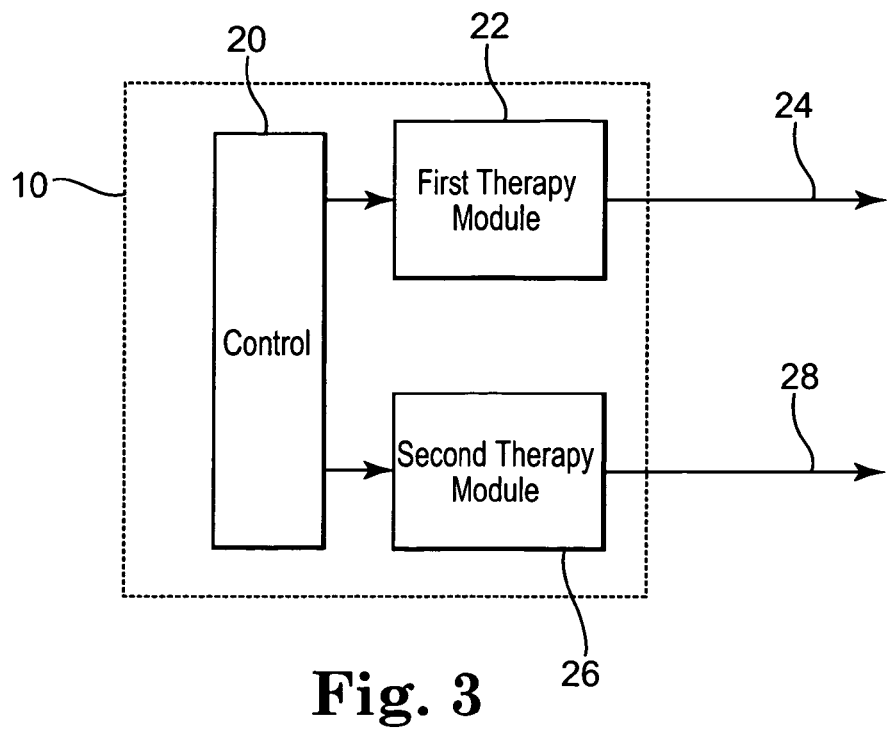
FIG. 3 is a general block diagram of a medical device having first and second therapy modules for the treatment of first and second neurological disorders.

FIG. 3 is a general block diagram of a portion of medical device 10 illustrating the concurrent treatment of multiple neurological disorders. Control 20 commands first therapy module 22 providing a first therapy output 24 and a second therapy module 26 providing a second therapy output 28. First therapy output 24 may provide a therapeutic output for a first neurological disorder and second therapy output 28 may provide a therapeutic output for a second neurological disorder. As noted above, first and second therapy outputs 24 and 28 may be electrical stimulation, drug infusion, thermal transducers or other therapeutic output. In general, a therapeutic output provides an advantageous benefit for a neurological disorder. Medical device 10 illustrated in FIG. 3 is depicted with both first therapy module 22 and second therapy module 26 operating open loop (for example, periodic), i.e., without feedback control. It is to be recognized and understood that either first therapy module 22 and/or second therapy module 26 could operate in closed loop (for example, responsive to a neurological event), i.e., with feedback control.

Figure 4:
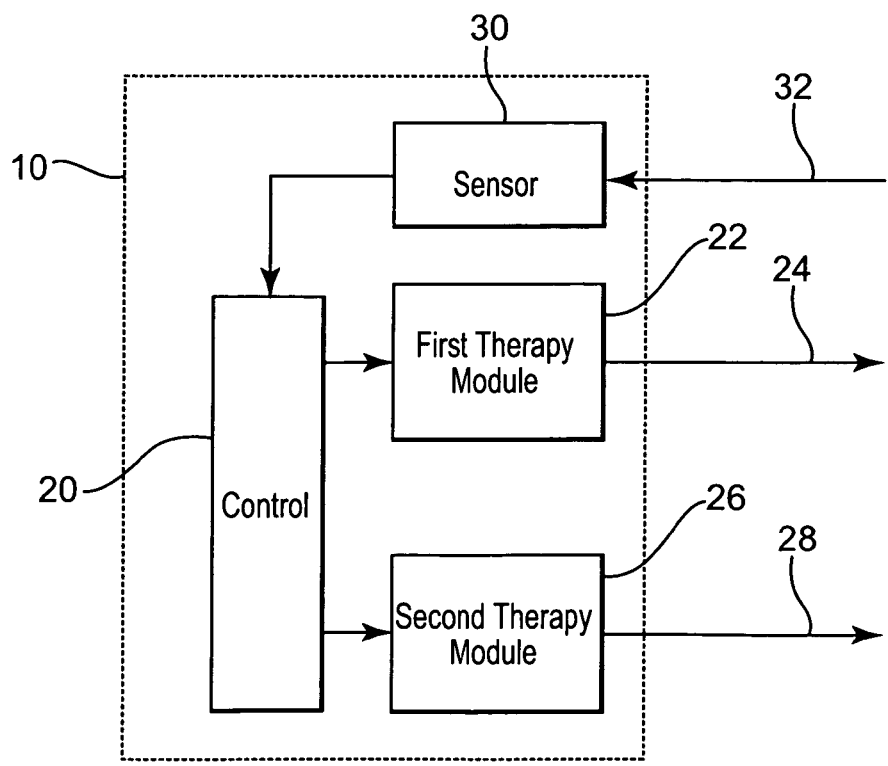
FIG. 4 is a general block diagram of a medical device having first and second therapy modules for the treatment of first and second neurological disorders using sensing for closed-loop feedback control.

This is illustrated in FIG. 4 in which medical device 10 employs sensor 30 sensing a condition on sensor lead 32. Control 20 may be responsive to sensor 30 and may cause either first therapy module 22 or second therapy module 26, or both, to operate in closed loop mode. It is to be recognized and understood that many different types of sensors are contemplated, including sensors that have not yet been developed. Sensors may include, but are not limited to, electrical signals, e.g., EEG or ECG, electrochemical feedback and movement sensors, e.g., accelerometers.

It is also possible that cross feedback may be employed between therapy modules. For example, if it is known that a first therapy, e.g., a drug infusion therapy, may be adversely impacted by a second therapy, e.g., an electrical stimulation pulse, then either the first or second therapy may be suspended for a time or for an event during the known activity of the other therapy. This is possible without relying on the sensed activity of the other therapy, through sensor 30, but may be achieved either in control 20, by direction connection between first therapy module 22 and second therapy module 26 or by direct feedback from either first therapy module 22 or second therapy module 26, or both.

Figure 5:
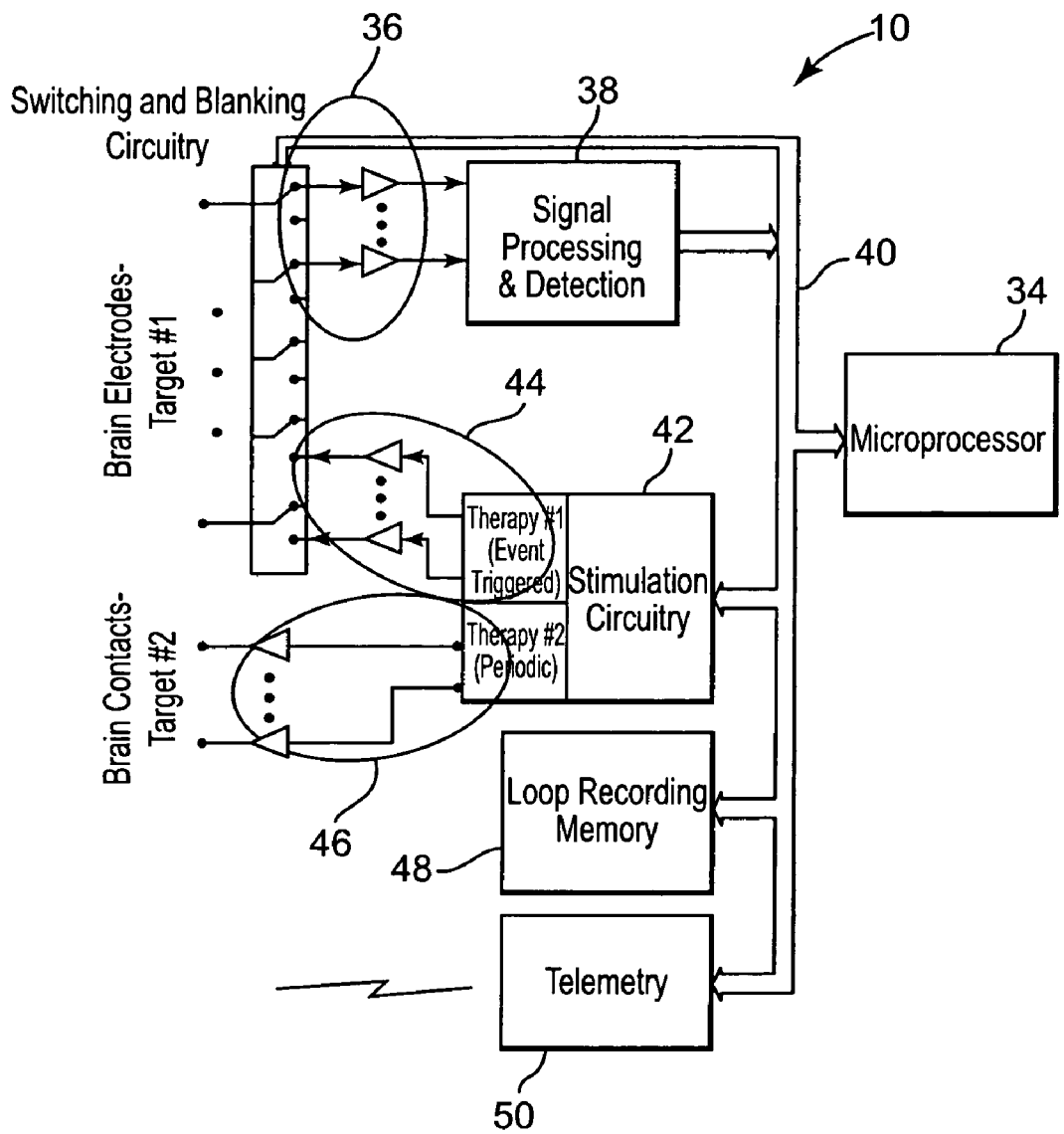
FIG. 5 is a detailed block diagram of a neurological stimulator having dual electrical stimulation therapeutic outputs.

FIG. 5 is a more detailed block diagram of medical device 10 controlled by microprocessor 34. Sensing circuitry 36 is used to detect or sense a condition of the body of patient 12. Sensed signals received are processed in signal processing and detection circuit 38, roughly equivalent to sensor 30 of FIG. 4, to analyze the sensed signal, signals or conditions received by sensing circuitry 36 and provide amplification, filtering, digitization and/or event detection. The output of signal processing and detection circuit 38 is passed via bi-directional bus 40 to microprocessor 34. Microprocessor 34 provides general command and control as well as timing, parameter setting and telemetry interface. Stimulation circuitry 42 receives control input from microprocessor 34 via bi-directional bus 40 and generates signals for electrical stimulation for delivery to patient 12 via first therapy output 44, e.g., an event triggered output, and via second therapy output 46, e.g., a periodic output. Stimulation circuitry 42 is capable of generating electrical stimulation pulses. Amplitude, pulse width, frequency and burst length are examples of commonly used parameters managed by stimulation circuitry 42. First therapy output 44 provides an electrical stimulation therapy for a first neurological disorder. Second therapy output 46 provides another electrical stimulation therapy for a second neurological disorder. Loop recording memory 48, coupled via bi-directional bus 40, provides memory for capturing sensor outputs and event detection outputs, for example. Telemetry module 50, also coupled via bi-directional bus 40, provides communication capability with an external device, e.g., programmer 18. Mechanical packaging, e.g., a biocompatible case, appropriate case and feedthroughs as well as electrical power are assumed and are not explicitly shown.

Figure 6:
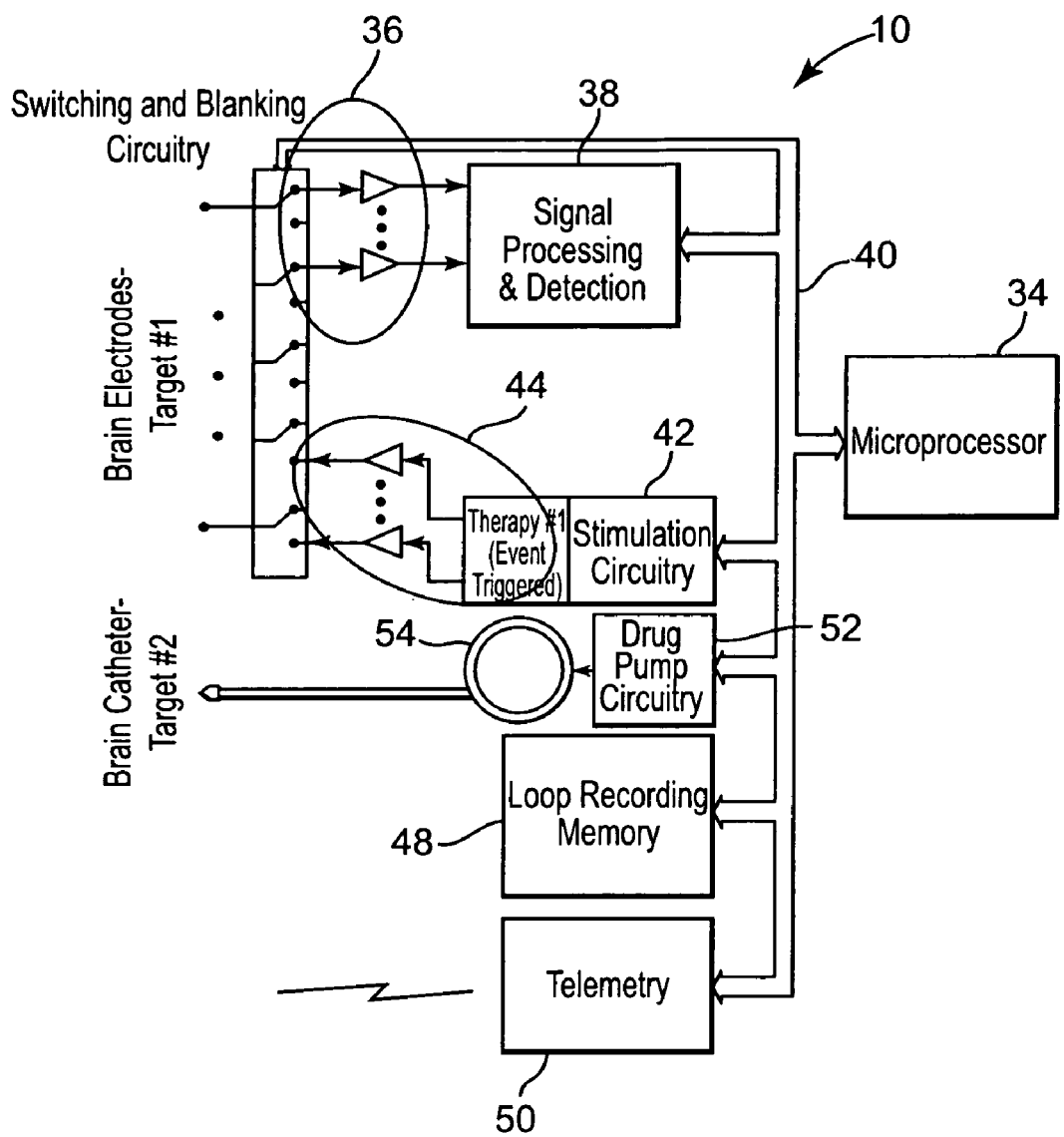
FIG. 6 is a detailed block diagram of a neurological stimulator having both electrical stimulation and drug infusion therapeutic outputs.

Medical device 10 illustrated in FIG. 6 is similar. However, stimulation circuitry 42 drives a single therapy output 44 that provides an electrical stimulation therapy for a first neurological disorder. Drug pump circuitry 52, coupled via bi-directional bus 40, drives drug infusion pump 52 providing a drug infusion therapy for a second neurological disorder instead of a second electrical stimulation therapy as illustrated and described with respect to FIG. 5. Drug pump circuitry 52 generally determines flow and could also control bolus injections.

While medical device 10 has been illustrated and described with respect to FIG. 5 and FIG. 6, it is to be recognized that other forms of therapy may be used instead of electrical stimulation and/or drug infusion therapy. As an example, thermal therapy, e.g., cooling, could be utilized for one or more of the therapies through a thermal transducer such as a Peltier junction device.

Medical device 10 can deliver therapy in open-loop, e.g., periodic, mode, in closed-loop, e.g., responsive to a neurological event, or a combination of open-loop and closed-loop modes. In the case of epilepsy and depression, closed-loop electrical stimulation may be delivered responsive to an ictal event while periodic stimulation or drug infusion may be delivered to reduce the symptoms of depression.

Figure 7:
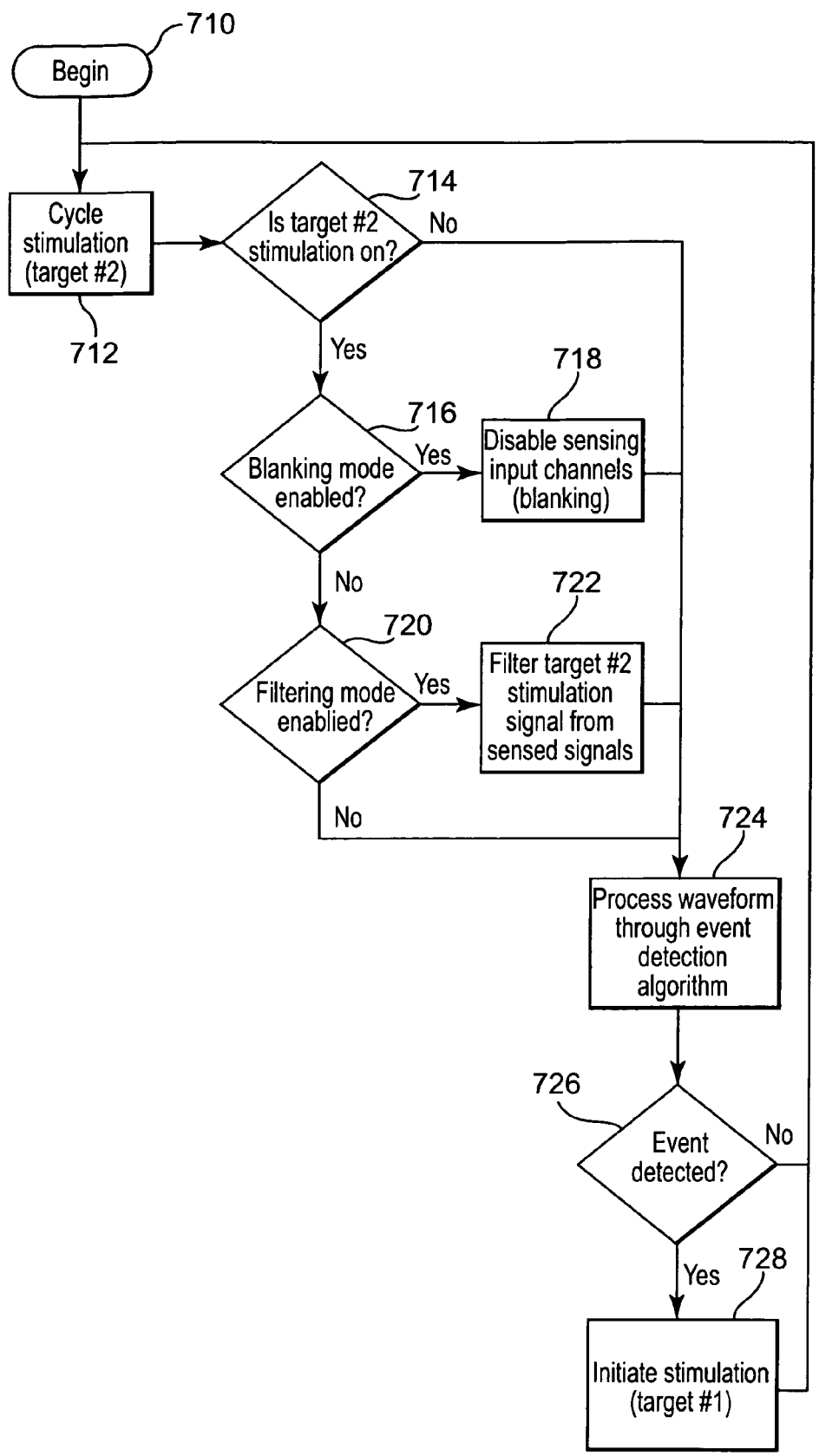
FIG. 7 is a flow chart illustrating aspects of control therapeutic output from a neurological stimulator.

The flow chart of FIG. 7 illustrates an embodiment of a therapy process implemented by an embodiment and a therapy process that could be implemented by medical device 10 illustrating an example of a combination of closed-loop therapy and open-loop therapy. In general, interaction between open-loop stimulation and sensing of ictal events should be carefully managed. It is generally undesirable for open-loop stimulation of the second therapy to cause an ictal event detection triggering a closed-loop stimulation output to the first therapy target. Such management may be handled by at least three ways as illustrated.

The process begins (710) and a cyclical stimulation (712) of target number 2, i.e., second therapy output 28. A determination (714) is made to see if the second therapy output is activated. If the second therapy output is deactivated, the process jumps to processing step 724. However, if second therapy output is activated, a determination (716) is made to see if blanking mode is enabled. If blanking is enabled, electrode inputs 36 to signal processing and detection circuit 38 are switched off, i.e., blanked, (718) during open-loop stimulation and, hence, event detection is disabled during the time of the actual active stimulation signal and the process jumps to processing step 724. Alternatively, a determination (720) is made to see if filtering mode is enabled. If filtering mode is enabled, the signal processing and detection circuit 38 continues to operate for event detection but the sensed signals from sensing circuitry 36 are filtered (722) for the open-loop second therapy output. This can be accomplished since it can be known the content, parameters and timing of the open-loop second therapy output. The specific open-loop second therapy signal is removed and the filtered signal is processed (724) through an event detection algorithm. Optionally, processing step 724 may only process the sensed signal if no or only a minimal open-loop second therapy output is present in the sensed signal, whether blanked and/or filtered or not. Either of these three techniques, or any combination or all of them, may be utilized to help ensure that the open-loop second therapy output signal does not materially affect the event detection algorithm. If desirable, any of these three modes of operation are selectable using external programmer 18.

If an event is detected (726), then the closed-loop first therapy output is initiated (728). If an event is not detected (726), then the process returns to determine (712) if the open-loop second therapy output is activated.

It may be desirable in certain circumstances that one of the therapies be a function of another therapy event. For example, if an ictal event is detected and a drug infusion therapy output is initiated, it may, in some circumstances, be desirable to temporarily suspend another therapy, e.g., open loop electrical stimulation for depression. Another reason for suspending electrical stimulation therapy, for example, might be because the electrical stimulation might adversely affect a drug being infused and/or the infusion process. In this case, electrical stimulation might be suspended for a predetermined period of time.

Thus, embodiments of invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device adapted to be implanted in a patient having a plurality of neurological disorders, comprising:
   a first therapy module providing a first output to said patient for the treatment of a first one of said plurality of disorders; and
   a second therapy module providing a second output to said patient for the treatment of a second one of said plurality of disorders;
   wherein said first therapy module and said second therapy module provide concurrent treatment of said plurality of neurological disorders.

2. An implantable medical device as in claim 1 wherein at least one of said first therapy module and said second therapy module is operative in a closed loop.

3. An implantable medical device as in claim 2 wherein another of said first therapy module and said second therapy module is operable in open loop.

4. An implantable medical device as in claim 2 wherein said at least one of said first output and said second output being a function of another of said first output and said second output.

5. An implantable medical device as in claim 2 further comprising a sensor detecting a sensed event from said patient associated with at least one of said plurality of neurological disorders and wherein at least one of said first therapy module and said second therapy module being operatively coupled to said sensor and being responsive to a sensed event from said patient.

6. An implantable medical device as in claim 1 wherein said first therapy module comprises a drug delivery module and wherein said first output comprises delivery of a medicament.

7. An implantable medical device as in claim 6 wherein said second therapy module comprises an electrical stimulator module and wherein said second output comprises an electrical stimulus signal.

8. An implantable medical device as in claim 7 wherein at least one of said drug delivery module and said electrical stimulator module is operative in a closed loop being responsive to the other of said drug delivery module and said electrical stimulator module.

9. An implantable medical device as in claim 7 further comprising a sensor detecting a sensed event from said patient, wherein at least one of said drug pump module and said electrical stimulator module is operatively coupled to said sensor and responsive to a sensed event from said patient.

10. An implantable medical device as in claim 1 wherein said first output and said second output are delivered based at least in part on cross feedback between said first therapy module and said second therapy module.

11. A method for the treatment of a plurality of neurological disorders in a patient using an implantable medical device having a first therapy module and a second therapy module, comprising the steps of:
provided a first output from said first therapy module to said patient for the treatment of a first one of said plurality of neurological disorders; and
providing a second output from said second therapy module to said patient for the treatment of a second one of said plurality of neurological disorders;
wherein said providing said first output step and providing said second output step provide concurrent treatment of said plurality of neurological disorders.

12. A method as in claim 11 wherein at least one of said first therapy module and said second therapy module is operated in a closed loop.

13. A method as in claim 12 wherein the other of said first therapy module and said second therapy module is operated in open loop.

14. A method as in claim 12 wherein said at least one of said first output and said second output being a function of another of said first output and said second output.

15. A method as in claim 12 further comprising the step of detecting a sensed event from said patient associated with at least one of said plurality of neurological disorders and operating at least one of said first therapy module and said second therapy module responsive to said sensed event.

16. A method as in claim 11 wherein said first therapy module comprises a drug delivery module and wherein said first output comprises delivery of a medicament.

17. A method as in claim 16 wherein said second therapy module comprises an electrical stimulator module and wherein said second output comprises an electrical stimulus signal.

18. A method as in claim 17 wherein at least one of said drug delivery module and said electrical stimulator module is operated in a closed loop being responsive to the other of said drug delivery module and said electrical stimulator module.

19. A method as in claim 17 further comprising the step of detecting a sensed event from said patient and wherein at least one of said drug pump module and said electrical stimulator module is responsive to said sensed event.

20. A method as in claim 11 further comprising the step of implanting said implantable medical device in said patient.

21. A method as in claim 11 wherein said providing said first output step and said providing said second output step occur based at least in part on cross feedback between said first therapy module and said second therapy module.

* * * * *